(12) United States Patent
Inoue et al.

(10) Patent No.: US 7,656,303 B2
(45) Date of Patent: Feb. 2, 2010

(54) GAS SENSOR SYSTEM WITH FAILURE DIAGNOSTIC FUNCTION AND FAILURE DIAGNOSIS METHOD FOR GAS SENSOR SYSTEM

(75) Inventors: Yoshinori Inoue, Nagoya (JP); Hiroshi Inagaki, Aichi (JP); Tomonori Uemura, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 262 days.

(21) Appl. No.: 11/748,720

(22) Filed: May 15, 2007

(65) Prior Publication Data

US 2007/0273540 A1    Nov. 29, 2007

(30) Foreign Application Priority Data

May 26, 2006    (JP)    ............................. 2006-146087

(51) Int. Cl.
*G08B 17/10*    (2006.01)

(52) U.S. Cl. ...................... 340/632; 340/514; 702/116
(58) Field of Classification Search ................ 340/632, 340/514, 633, 634; 702/116; 204/424, 425, 204/426; 60/285, 276, 277; 701/109
See application file for complete search history.

(56) References Cited

U.S. PATENT DOCUMENTS

| | | | | |
|---|---|---|---|---|
| 6,089,016 A | * | 7/2000 | Takaku | 60/277 |
| 6,093,294 A | * | 7/2000 | Kato et al. | 204/425 |
| 6,136,169 A | | 10/2000 | Okamoto | |
| 6,210,641 B1 | * | 4/2001 | Yamada et al. | 422/94 |
| 2004/0222094 A1 | * | 11/2004 | Ieda et al. | 204/424 |
| 2006/0157348 A1 | | 7/2006 | Inoue et al. | |

FOREIGN PATENT DOCUMENTS

| | | |
|---|---|---|
| JP | 11-107830 A | 4/1999 |
| JP | 2003-97342 A | 4/2003 |
| JP | 2006-208363 A | 8/2006 |

* cited by examiner

*Primary Examiner*—Anh V La
(74) *Attorney, Agent, or Firm*—Sughrue Mion, PLLC

(57) ABSTRACT

A gas sensor system includes a gas sensor capable of producing an output signal responsive to the concentration of a specific gas component in measurement gas, a gas concentration determination device that makes electrical connections to the gas sensor and determines the concentration of the specific gas component according to the output signal of the gas sensor, a failure detection device that detects a potential failure in any one of the electrical connections, a sensor temperature determination device that judges whether the gas sensor has been cooled to a predetermined temperature or lower with reference to a sensor temperature parameter and a failure identification device that, when the gas sensor has been cooled to the predetermined temperature or lower, outputs a diagnosis signal to the gas sensor, measures potentials of the electrical connections under the diagnosis signal and identifies in which of the electrical connections the potential failure is occurring based on the measured potentials.

6 Claims, 3 Drawing Sheets

GAS SENSOR SYSTEM WITH FAILURE DIAGNOSTIC FUNCTION AND FAILURE DIAGNOSIS METHOD FOR GAS SENSOR SYSTEM

BACKGROUND OF THE INVENTION

The present invention relates to a gas sensor system with a failure diagnostic function and a failure diagnosis method for a gas sensor system.

Heretofore, an internal combustion engine such as a gasoline engine has adopted, as a combustion control technique for reductions in automotive CO, NOx and HC emissions, air-fuel ratio feedback control by regulating fuel injection in accordance with the concentration of a specific gas component in exhaust gas. There are various exhaust gas sensors for use in air-fuel ratio control. One example of exhaust gas sensor is an oxygen sensor having a single electrochemical cell, which consists of a solid electrolyte layer and a pair of electrodes arranged on opposite sides of the solid electrolyte layer and exposed to measurement gas and reference gas, respectively, so as to detect the concentration of oxygen in the measurement gas based on a potential difference between the measurement gas and the reference gas. Another example of exhaust gas sensor is an air-fuel ratio sensor (also called a "full-range oxygen sensor") having two electrochemical cells with a measurement gas chamber defined between these two cells to introduce measurement gas into the measurement gas chamber through a gas diffusion material and detect the concentration of oxygen in the measurement gas linearly over rich and lean ranges. A NOx sensor with three electrochemical cells is also known as the exhaust gas sensor. Each of these exhaust gas sensors is generally equipped or combined with a heater in order to activate the electrochemical cell irrespective of the exhaust gas temperature.

It has recently become common practice to form an automotive gas sensor system with a gas sensor and a sensor control unit and to diagnose the occurrence of a failure in the gas sensor or the sensor control unit automatically during engine combustion control. Japanese Laid-Open Patent Publication No. 11-107830 and No. 2003-097342 propose gas sensor systems of such failure diagnostic type, each of which is configured to diagnose a system failure e.g. a short-circuit or wire breakage and then inform a vehicle driver of the diagnosis result.

SUMMARY OF THE INVENTION

The failure diagnosis is carried out by e.g. measuring a potential difference (voltage) between the cell electrodes with the passage of an electric current when the electrochemical cell is held in an active state. However, the electrochemical cell is too low in internal resistance (about several tens to 100Ω) during the active state to develop a sufficient amount of potential difference between the cell electrodes for system failure diagnosis. In the case of the electrochemical cell having an internal resistance of 30Ω, for example, there arises a small voltage drop of 0.3 V between the cell electrodes by the passage of a diagnosis current of 10 mA under conditions where one of the cell electrodes is shorted to ground potential. Because of such a small potential difference, the gas sensor system fails to identify which of the cell electrodes is being shorted to ground potential.

In order to avoid this diagnosis problem, it is conceivable to apply a larger amount of diagnosis current through the electrochemical cell during the active state. The gas sensor system however has to employ a larger-capacity current source for the application of the large diagnosis current, thereby resulting in cost increases. The application of the large diagnosis current also hastens deterioration or breakdown of the electrochemical cell.

It is therefore an object of the present invention to provide a gas sensor system capable of performing a system failure diagnostic function assuredly without cost increase and cell deterioration/breakdown.

It is also an object of the present invention to provide a failure diagnosis method for a gas sensor system.

According to one aspect of the present invention, there is provided a gas sensor system with a failure diagnostic function, comprising: a gas sensor capable of producing an output signal responsive to the concentration of a specific gas component in measurement gas; a gas concentration determination device that makes electrical connections to the gas sensor and determines the concentration of the specific gas component according to the output signal of the gas sensor; a failure detection device that detects the occurrence of a potential failure in any one of the electrical connections; a sensor temperature determination device that judges whether the gas sensor has been cooled to a predetermined temperature or lower with reference to a sensor temperature parameter; and a failure identification device that, when the gas sensor is judged as being cooled to the predetermined temperature or lower, outputs a diagnosis signal to the gas sensor, measures potentials of the respective electrical connections under the diagnosis signal and identifies the any one of the electrical connections in which the potential failure is occurring based on the measured potentials.

According to another aspect of the present invention, there is provided a failure diagnosis method for a gas sensor system, the gas sensor system having a gas sensor capable of producing an output signal responsive to the concentration of a specific gas component in measurement gas and a gas concentration determination device that makes electrical connections to the gas sensor and determines the concentration of the specific gas component according to the output signal of the gas sensor, the failure diagnosis method comprising: detecting the occurrence of a potential failure in any one of the electrical potentials; judging whether the gas sensor has been cooled to a predetermined level or lower with reference to a sensor temperature parameter; when the gas sensor is judged as being cooled to the predetermined level or lower, outputting a diagnosis signal to the gas sensor; measuring potentials of the respective electrical connections under the diagnosis signal; and identifying the any one of the electrical connections in which the potential failure is occurring based on the measured potentials.

The other objects and features of the present invention will also become understood from the following description.

DESCRIPTION OF THE EMBODIMENTS

The present invention will be described below with reference to the drawings.

Figure 1A:
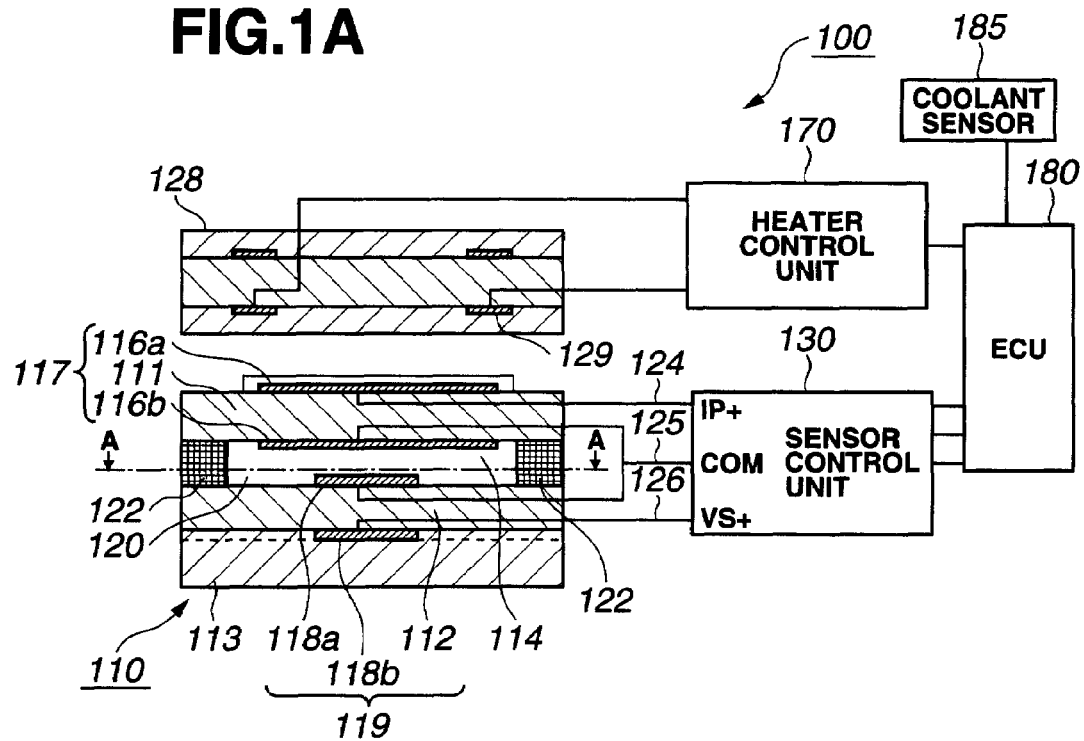
FIG. 1A is a schematic view of a gas sensor system according to one exemplary embodiment of the present invention.

Referring to FIG. 1A, a gas sensor system 100 for an automotive internal combustion engine according to one exemplary embodiment of the present invention includes a gas sensor 110 integral with or separate from a heater 128, a sensor control unit 130, a heater control unit 170, an engine control unit (ECU) 180, a temperature sensor 185 and electric wires 124, 125 and 126.

The gas sensor 110 is mounted on an exhaust pipe of the engine so as to produce an output according to the concentration of a specific gas component in exhaust gas. The gas sensor 110 can be of any type such as a single-cell oxygen sensor (inclusive of a limiting-current type oxygen sensor), a two-cell air-fuel ratio sensor (called a full-range oxygen sensor) or a three-cell NOx sensor. In the present embodiment, the gas sensor 110 is a full-range air-fuel ratio sensor capable of producing a current signal linearly responsive to the concentration of oxygen in the exhaust gas (i.e. responsive to the air-fuel ratio of the engine).

Figure 1B:
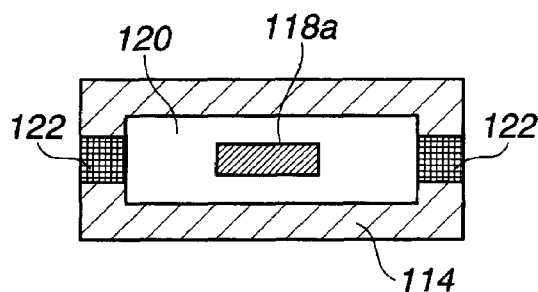
FIG. 1B is a section view of a gas sensor, when cut along a line A-A of FIG. 1A, according to one exemplary embodiment of the present invention.
Figure 2:
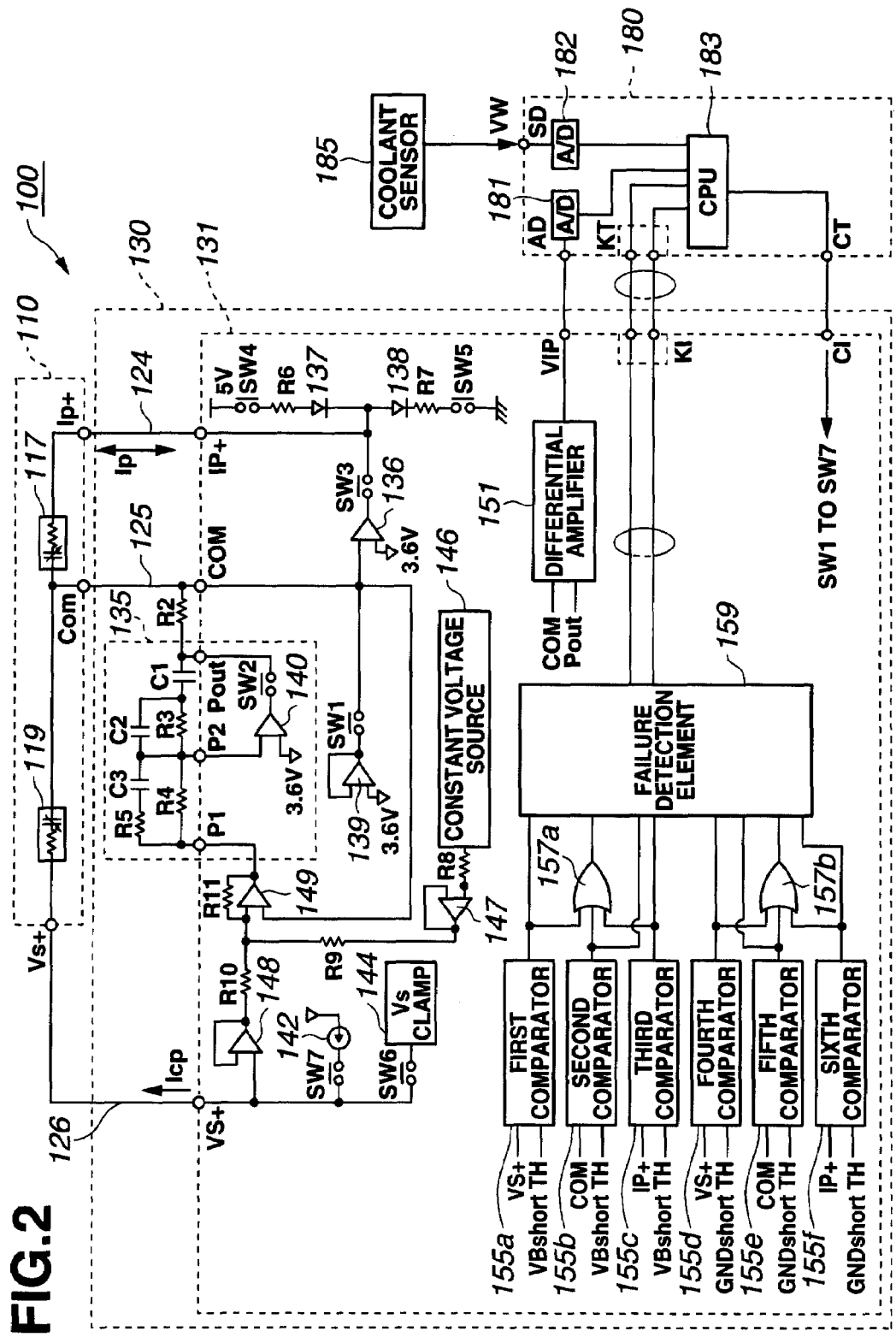
FIG. 2 is a circuit diagram of the gas sensor system according to one exemplary embodiment of the present invention.

As shown in FIGS. 1A and 2, the gas sensor 110 is electrically connected at terminals Ip+, Com and Vs+ to terminals IP+, COM and VS+ of the sensor control unit 130 via the electric wires 124, 125 and 126. Further, the gas sensor 110 has thin solid electrolyte layers 111 and 112, an insulating layer 114, a reinforcing plate 113, first and second pairs of porous electrodes 116a, 116b, 118a and 118b and a gas diffusion layer 122 as shown in FIGS. 1A and 1B.

The solid electrolyte layers 111 and 112 are made of oxygen ion conductive zirconia ($ZrO_2$). The insulating layer 114 is made of alumina ($Al_2O_3$) and laminated between the solid electrolyte layers 111 and 112 to keep the solid electrolyte layers 111 and 112 electrically insulated from each other. For example, the solid electrolyte layers 111 and 112 and the insulating layer 114 can be formed by sintering green sheets of zirconia and a paste or green sheet of alumina, respectively. The reinforcing plate 113 is attached externally to the solid electrolyte layer 112 for reinforcement of the laminate of these layers 111, 114 and 112.

The porous electrodes 116a and 116b are arranged on opposite sides of the solid electrolyte layer 111 to form a pumping cell 117, whereas the porous electrodes 118a and 118b are arranged on opposite sides of the solid electrolyte layer 112 to form a sensing cell 119. The electrical connection between the porous electrodes 116b and 118a and the sensor control unit 130 is made by the sensor terminal Com, the electric wire 125 and the circuit terminal COM for the application of a common reference voltage (sensor control voltage) from the sensor control unit 130 to the pumping cell 117 and the sensing cell 119. On the other hand, the electrical connection between the porous electrode 116a and the sensor control unit 130 is made by the sensor terminal Ip+, the electric wire 124 and the circuit terminal IP+ for the passage of an electric current Ip from the sensor control unit 130 to the pumping cell 117. The electrical connection between the porous electrode 118b and the sensor control unit 130 is made by the sensor terminal Vs+, the electric wire 126 and the circuit terminal VS+ for the application of a constant electric current Icp from the sensor control unit 130 to the sensing cell 119 in a direction from the electrode 118b to the electrode 118a.

There is a measurement gas chamber 120 defined by the pumping cell 117, the sensing cell 119 and the insulating layer 114 with the porous electrodes 116b and 118a being exposed to the measurement gas chamber 120.

The gas diffusion layer 122 is arranged between the solid electrolyte layers 111 and 112 so that the measurement gas chamber 120 is in gas communication with the outside of the gas sensor 110 through the gas diffusion layer 122. To diffuse a regulated amount of exhaust gas into the measurement gas chamber 120, the gas diffusion layer 122 is made of a porous sintered material having gas diffusion pores.

As shown in FIG. 1A, the heater 128 has a plate-shape with one side of the heater 128 facing the solid electrolyte layer 110 and incorporates therein a wiring arrangement 129 to heat the gas sensor 110 to 600 to 900° C. The heater control unit 170 is electrically connected with and operated under the control of signals from the ECU 180 in such a manner as to control the supply of power from a battery to the heater 128 by PWM control and thereby maintain the temperature of the gas sensor 110 at 600 to 900° C.

When the pumping cell 117 and the sensing cell 119 are held at 600 to 900° C., each of the pumping cell 117 and the sensing cell 119 enters an active state where the solid electrolyte layer 111, 112 allows oxygen ion conduction therethrough. During the active state, the pumping cell 117 performs its oxygen pumping action by the passage of the pumping cell current Ip so as to feed oxygen into or out of the measurement gas chamber 120. In view of the fact that the amount and direction of flow of the pumping cell current Ip varies depending on the oxygen concentration of the exhaust gas as will be explained later, the pumping cell current Ip is taken as the output signal of the gas sensor 110. The sensing cell 119 also performs its oxygen pumping action during the active state by the passage of the constant current Icp so that the porous electrode 118b functions as a self-regulating reference electrode to accumulate a nearly constant concentration of oxygen as reference gas. As a result, there arises a voltage as electromotive force across the sensing cell 119 in accordance with a difference in oxygen concentrations between the sensing cell electrode 118b and the measurement gas chamber 120. The electromotive voltage of the sensing cell 119 is outputted as a feedback from the gas sensor 110 to the sensor control unit 130.

The sensor control unit 130 controls the operations of the gas sensor 110 under the control of the ECU 180 while processing the output signal of the gas sensor 110 into a voltage signal indicative of the exhaust oxygen concentration and outputting the voltage signal to the ECU 180. The sensor control unit 130 further generates a diagnosis signal to the gas sensor 110, reads potentials of the respective electrical connections between the gas sensor 110 and the sensor control unit 130 (e.g. potentials at the circuit terminals VS+, COM and IP+), and then, outputs information about the potentials of the electrical connections between the gas sensor 110 and the sensor control unit 130.

The temperature sensor 185 provides a sensor temperature parameter for judgment about the heating/cooling condition of the gas sensor 110. There is no particular restriction on the sensor temperature parameter as long as it can be judged by the sensor temperature parameter whether the gas sensor 110 has been activated or cooled to a predetermined temperature or lower. Although the temperature of the gas sensor 110 itself could conceivably be used as the sensor temperature parameter, there is a possibility that the temperature of the gas sensor 110 may not be measured accurately in the event of a failure in the gas sensor 110. For this reason, it is desirable to use e.g. engine coolant temperature, exhaust gas temperature or sensor heater temperature as the sensor temperature parameter. In the present embodiment, the temperature sensor 185 is a coolant sensor mounted on the engine to produce a signal VW responsive to the coolant temperature of the engine. The engine coolant temperature becomes relatively high during engine operations and tends to change with the temperature of the gas sensor 110. Namely, the engine coolant temperature can be suitably used as the sensor temperature parameter for easy judgment about the heating/cooling condition of the gas sensor 110.

The ECU 180 is electrically connected at terminals AD, KT and CT to terminals VIP, KI and CI of the sensor control unit 130 for signal transmissions between the sensor control unit 130 and the ECU 180. The ECU 180 is also electrically connected at an input terminal VW to the coolant sensor 185 for signal transmission from the coolant sensor 185 to the ECU 180. As shown in FIG. 2, the ECU 180 has two AD converters 181 and 182 and a CPU 183. The AD converter 181 receives the oxygen concentration signal from the sensor control unit 130 through the terminals VIP and AD and digitizes the oxygen concentration signal. The AD converter 182 receives the coolant temperature signal VW from the coolant sensor 185 through the terminals VW and digitizes the coolant temperature signal. The CPU 183 determines engine operation parameters such as exhaust oxygen concentration, engine air-fuel ratio and coolant temperature based on these digitized signals. The CPU 183 further receives the connection potential information from the sensor control unit 130 through the terminals KI and KT by serial transmissions, diagnoses the occurrence of a potential failure in any of the electrical connections between the gas sensor 110 and the sensor control unit 130 with reference to the connection potential information and the engine coolant temperature, and then, outputs control signals (switch on-off signals) through the terminals CT and CI to control the operations of the sensor control unit 130 according to the diagnosis result.

In the present embodiment, the ECU 180 accordingly functions, together with the temperature sensor 185, as a sensor temperature detection device that judges whether the gas sensor 110 has been activated or cooled to the predetermined temperature or lower with reference to the sensor temperature parameter. On the other hand, the sensor control unit 130 and the ECU 180 function together as a gas concentration determination device that determines the oxygen concentration of the exhaust gas according to the output signal of the gas sensor 110, a failure detection device that performs a failure detection step to detect the potential failure in any of the electrical connections between the gas sensor 110 and the sensor control unit 130 (gas concentration determination device) and a failure identification device that performs a failure identification step to, when the gas sensor 110 is judged as being cooled to the predetermined temperature or lower, output the diagnosis signal to the gas sensor 110, measure the potentials of the electrical connections between the gas sensor 110 and the sensor control unit 130 under the diagnosis signal and then identify in which of these electrical connections the potential failure is occurring.

The internal resistance of the gas sensor 110 is very low when the gas sensor 110 is in a high-temperature (activation) state. When the gas sensor 110 is in a low-temperature state, by contrast, the internal resistance of the gas sensor 110 becomes so high that there arises a relatively large potential difference across each of the electrical connections between the gas sensor 110 and the sensor control unit 130 even by the output of the diagnosis signal of small amplitude. It is thus possible in such a low-temperature state to carry out concrete diagnosis about the potential failure in each of the electrical connections between the gas sensor 110 and the sensor control unit 130 properly and assuredly without deterioration and breakage of the gas sensor 110 by controlling the diagnosis signal to within safe limits.

The failure detection step is performed to detect the potential failure in any of the electrical connections between the gas sensor 110 and the sensor control unit 130 but not to identify in which of these electrical connections the potential failure is occurring. There is no particular restriction on the timing of the failure detection step. The failure detection step can be performed when the gas sensor 110 is in the high-temperature (activation) state or in the low-temperature state. Further, the failure detection step can be performed before or after judging the gas sensor 110 as being cooled to the predetermined temperature or lower.

The failure identification step is performed to identify in which of the electrical connections between the gas sensor 110 and the sensor control unit 130 the potential failure is occurring based on the potentials of these electrical connections under the diagnosis signal.

The diagnosis signal can be either a current signal or a voltage signal. In the case of the diagnosis signal being a current signal, it is preferable to control the diagnosis signal to 30 mA or smaller, more preferably 20 mA or smaller, in order to prevent the gas sensor 110 from becoming deteriorated or broken by the output of the diagnosis current.

There is no particular restriction on the process of the failure identification step. For example, the failure identification step can be performed by making comparisons among the potentials of the electrical connections and deciding that one of the electrical connections highest in potential is shorted to battery potential and that the other one of the electrical connections lowest in potential is shorted to ground potential. For more proper and concrete failure diagnosis, the failure identification step is preferably performed by comparing each of the potentials of the electrical connections with upper and lower limit thresholds and deciding that the electrical connection higher in potential than the upper limit threshold is shorted to battery potential and that the electrical connection lower in potential than the lower limit threshold is shorted to ground potential.

It is preferable to once disconnect the gas sensor 110 from a power supply circuit of the sensor control unit 130 and cut off voltage/current supply from the power supply circuit to the gas sensor 110 upon detection of the potential failure in any of the electrical connection between the gas sensor 110 and the sensor control unit 130 in the failure detection step and, when the gas sensor 110 is judged as being cooled to the predetermined temperature or lower, connect the gas sensor 110 to a part of the power supply circuit and then perform the failure identification step. In this case, the gas sensor 110 is protected from excessive current flow or current flow in the wrong direction and prevented from deterioration or breakage more assuredly in the event that the any of the electrical connections is shorted to battery potential or ground potential.

More specifically, the sensor control unit 130 includes a sensor control circuit 131 and a detection resistor R2 externally added to the sensor control circuit 131 as shown in FIG. 2 in the present embodiment. These electronics 131 and R2 are mounted on a single circuit board.

The sensor control circuit 131 has an ASIC configuration with amplifiers 136, 147, 148 and 149, resistor R8, R9, R10 and R11, a constant current source 142, a voltage clamp 144, a constant voltage source 146, a PID controller 135, a differential amplifier 151 and switches SW2, SW3, SW6 and SW7 for gas concentration detection.

The constant current source 142 is connected to the circuit terminal VS+ via the switch SW7 to supply the constant current Icp to the sensing cell 119 through the circuit terminal VS+, the electric wire 126 and the sensor terminal Vs+ and thereby maintain the oxygen concentration of the sensing cell electrode 118b constant as explained above. The output Icp of the constant current source 142 is turned on and off by the switch SW7. The voltage clamp 144 is connected to the circuit terminal VS+ via the switch SW6 to set an upper limit on the voltage of the circuit terminal VS+. The output of the voltage clamp 144 is turned on and off by the switch SW6.

The amplifier 136 has an inverting input terminal connected to the circuit terminal COM, a non-inverting input terminal connected to a reference voltage of 3.6 V and an output terminal connected to the circuit terminal IP+ via the switch SW3, thereby forming a negative feedback loop to feed the pumping cell current Ip through the circuit terminal IP+, the electric wire 124 and the sensor terminal Ip+. The output Ip of the amplifier 136 is turned on and off by the switch SW3.

The PID controller 135 has resistors R3, R4 and R5, capacitors C1, C2 and C3 and an amplifier 140 to improve the pumping cell current control characteristics of the negative feedback loop by PID operation. The resistors R3, R4 and R5 and the capacitors C1, C2 and C3 are arranged to define the control parameters of the PID controller 135. The amplifier 140 has an inverting input terminal connected to a terminal P2 of the sensor control circuit 130, a non-inverting input terminal connected to a reference voltage of 3.6 V and an output terminal connected to an output terminal Pout of the PID controller 135 via the switch SW2 so that the output of the PID controller 135 is turned on and off by the switch SW2.

The input terminal P1 of the PID controller 135 is connected to the circuit terminal VS+ through the amplifiers 148 and 149 and to the constant voltage source 146 through the amplifiers 147 and 149, whereas the output terminal Pout of the PID controller 135 is connected to the inverting input terminal of the amplifier 136 via the detection resistor R2. The amplifier 147 has an inverting input terminal and an output terminal connected to each other and a non-inverting input terminal connected to the constant voltage source 146 via the resistor R8. The amplifier 148 has an inverting input terminal and an output terminal connected to each other and a non-inverting input terminal connected to the circuit terminal VS+. The amplifier 149 has an inverting input terminal and an output terminal connected to each other via the resistor R11 and a non-inverting input terminal connected to the circuit terminal COM. The inverting input terminal of the amplifier 149 is also connected to the output terminal of the amplifier 147 via the resistor R9 and to the output terminal of the amplifier 148 via the resistor R10. The output terminal of the amplifier 149 is also connected to the input terminal P1 of the PID controller 135. Further, the constant voltage source 146 supplies a control target voltage of 450 mV as a control target value of the output voltage of the sensing cell 119. The PID controller 135 thus receives the output voltage of the sensing cell 119 and the control target voltage of the voltage source 146 and performs PID operation on a difference ΔVs+ between the output voltage of the sensing cell 119 and the control target voltage of the voltage source 146 to provide feedback for the control of the pumping cell current Ip.

The differential amplifier 151 has input terminals connected to the respective circuit terminals COM and Pout (although connection lines are omitted in the drawing) and an output terminal connected to the circuit terminal VIP to amplify a voltage difference developed across the detection resistor R2 by the passage of the pumping cell current Ip, i.e., to convert the pumping cell current Ip to the oxygen concentration signal (voltage signal).

In the case where the measurement gas (exhaust gas) is fuel-rich, the concentration of oxygen in the measurement gas chamber 120 of the gas sensor 110 is lower than a stoichiometric air-fuel ratio level so that the output voltage of the sensing cell 119 becomes higher than the control target voltage (450 mV). Then, the PID controller 135 performs PID operation on the difference ΔVs+ between the sensing cell output voltage and the control target voltage. The amplifier 136 feeds the current Ip through the pumping cell 117 according to the feedback from the PID controller 135 in such a manner as to introduce a shortfall of oxygen into the measurement gas chamber 120 and adjust the oxygen concentration of the measurement gas chamber 120 to the stoichiometric air-fuel ratio level by the oxygen pumping action of the pumping cell 117. In the case where the measurement gas (exhaust gas) is fuel-lean, by contrast, the concentration of oxygen in the measurement gas chamber 120 of the gas sensor 110 is higher than the stoichiometric air-fuel ratio level so that the output voltage of the sensing cell 119 becomes lower than the control target voltage value (450 mV). The PID controller 135 then performs PID operation on the difference ΔVs+ between the sensing cell output voltage and the control target voltage. The amplifier 136 feeds the current Ip through the pumping cell 117 according to the feedback from the PID controller 135 in such a manner as to releases an excess of oxygen from the measurement gas chamber 120 and adjust the oxygen concentration of the measurement gas chamber 120 to the stoichiometric air-fuel ratio level by the oxygen pumping action of the pumping cell 117. Accordingly, the exhaust oxygen concentration can be determined by measuring the pumping cell current Ip, and more specifically, the voltage across the detection resistor R2.

The sensor control circuit 131 further includes amplifiers 137, 138 and 139, resistors R6 and R7, first to sixth comparators 155a to 155f, first and second OR gates 157a and 157b, a failure detection element 159 and switches SW1, SW4 and SW5 for system failure diagnosis.

The amplifier 139 has an inverting input terminal and an output terminal connected to each other and a non-inverting input terminal connected to a reference voltage of 3.6 V. The output terminal of the amplifier 139 is also connected to the circuit terminal COM via the switch SW1 and to the non-inverting input terminal of the amplifier 136. Through these connections, the amplifier 139 feeds a weak diagnosis current as the diagnosis signal to the pumping cell 117 and the sensing cell 119. The output of the amplifier 139 is turned on and off by the switch SW1.

The resistor R6 has one end connected to the circuit terminal IP+ via the diode 137 and the other end connected to the switch SW4, whereas the resistor R7 has one end connected to the circuit terminal IP+ via the diode 138 and the other end connected to the switch SW5. Both of the resistors R6 and R7 function as voltage dividers to divide a reference voltage of 5 V in half and output a voltage of 2.5 V forcibly to the circuit terminal IP+ through the diodes 137 and 138 upon detection of the potential failure. The outputs of the resistors R6 and R7 are turned on and off by the switches SW4 and SW5.

The first to sixth comparators 155a to 155f are arranged to check whether the potentials of the circuit terminals VS+, COM and IP+ are maintained within given limits as follows.

The first comparator 155a has two input terminals: one input terminal connected to the circuit terminal VS+ and the other input terminal connected to an upper threshold voltage VBshort (although connection lines are omitted in the drawing) and an output terminal connected to an input terminal of the first OR gate 157a. The fourth comparator 155d has one input terminal connected to the circuit terminal VS+, the other input terminal connected to a lower threshold voltage GNDshort and an output terminal connected to an input terminal of the second OR gate 157b. The upper threshold voltage VBshort of the first comparator 155a and the lower threshold voltage GNDshort of the fourth comparator 155d are set to predetermined voltage values. Under normal conditions, the potential of the circuit terminal VS+ is held at 4.05 V, i.e., the sum of the reference voltage (3.6V) of the circuit terminal COM and the output voltage (450 mV) of the sensing cell 119. In the present embodiment, the upper threshold voltage VBshort of the first comparator 155a is thus set to e.g. 9 V. Alternatively, the upper threshold voltage VBshort of the first comparator 155a may be set by subtracting an ASIC power supply voltage by a given value (e.g. 1.5 V) in view of fluctuations in power supply voltage. Further, the lower threshold voltage GNDshort of the fourth comparator 155d is set to e.g. 1 V in view of fluctuations in ground potential (0 V) in the present embodiment. The first comparator 155a reads the potential of the circuit terminal VS+, compares the potential of the circuit terminal VS+ with the upper threshold voltage VBshort and, when the potential of the circuit terminal VS+ is higher than the upper threshold voltage VBshort, generates a failure signal (high-level signal) indicating the occurrence of the potential failure in which the circuit terminal VS+ (or the sensor terminal Vs+ or the electric wire 126) is shorted to battery potential. The fourth comparator 155d concurrently reads the potential of the circuit terminal VS+, compares the potential of the circuit terminal VS+ with the lower threshold voltage GNDshort and, when the potential of the circuit terminal VS+ is lower than the lower threshold voltage GNDshort, generates a failure signal (high-level signal) indicating the occurrence of the potential failure in which the circuit terminal VS+ (or the sensor terminal Vs+ or the electric wire 126) is shorted to ground potential. The failure signals of the first and fourth comparators 155a and 155d are outputted to the first and second OR gates 157a and 157b and the failure detection element 159.

Similarly, the second comparator 155b has one input terminal connected to the circuit terminal COM, the other input terminal connected to an upper threshold voltage VBshort and an output terminal connected to an input terminal of the first OR gate 157a. The fifth comparator 115e has one input terminal connected to the circuit terminal COM, the other input terminal connected to a lower threshold voltage GNDshort and an output terminal connected to an input terminal of the second OR gate 157b. The potential of the circuit terminal COM is held at 3.6 V (reference voltage) by the amplifier 136 under normal conditions. The upper threshold voltage VBshort of the second comparator 155b and the lower threshold voltage GNDshort of the fifth comparator 155e are thus set to e.g. 9 V and 1 V, respectively, in the same way as above. The second comparator 155b reads the potential of the circuit terminal COM, compares the potential of the circuit terminal COM with the upper threshold voltage VBshort and, when the potential of the circuit terminal COM is higher the upper threshold voltage VBshort, generates a failure signal (high-level signal) indicating the occurrence of the potential failure in which the circuit terminal COM (or the sensor terminal Corn or the electric wire 125) is shorted to battery potential. The fifth comparator 155e concurrently reads the potential of the circuit terminal COM, compares the potential of the circuit terminal COM with the lower threshold voltage GNDshort and, when the potential of the circuit terminal COM is lower than the lower threshold voltage GNDshort, generates a failure signal (high-level signal) indicating the occurrence of the potential failure in which the circuit terminal COM (or the sensor terminal Corn or the electric wire 125) is shorted to ground potential. The failure signals of the second and fifth comparators 155b and 155e are outputted to the first and second OR gates 157a and 157b and then to the failure detection element 159.

The third comparator 155c has one input terminal connected to the circuit terminal IP+, the other input terminal connected to an upper threshold voltage VBshort and an output terminal connected to an input terminal of the first OR gate 157a. The sixth comparator 155f has one input terminal connected to the circuit terminal IP+, the other input terminal connected to a lower threshold voltage GNDshort and an output terminal connected to an input terminal of the second OR gate 157b. The potential of the circuit terminal IP+ is also held at 3.6 V (reference voltage) under normal conditions. The upper threshold voltage VBshort of the third comparator 155c and the lower threshold voltage GNDshort of the sixth comparator 155f are thus set to e.g. 9 V and 1 V, respectively, in the same way as above. The third comparator 155c reads the potential of the circuit terminal IP+, compares the potential of the circuit terminal IP+ with the upper threshold voltage VBshort and, when the potential of the circuit terminal IP+ is higher the upper threshold voltage VBshort, generates a failure signal (high-level signal) indicating the occurrence of the potential failure in which the circuit terminal IP+ (or the sensor terminal Ip+ or the electric wire 124) is shorted to battery potential. The sixth comparator 155f concurrently reads the potential of the circuit terminal IP+, compares the potential of the circuit terminal IP+ with the lower threshold voltage GNDshort and, when the potential of the circuit terminal IP+ is lower than the lower threshold voltage GNDshort, generates a failure signal (high-level signal) indicating the occurrence of the potential failure in which the circuit terminal IP+ (the sensor terminal Ip+ or the electric wire 124) is shorted to ground potential. The failure signals of the third and sixth comparators 155c and 155f are outputted to the first and second OR gates 157a and 157b and then to the failure detection element 159.

The first OR gate 157a implements logical OR operation of the failure signals from the first to third comparators 155a to 155c. Upon receipt of the failure signal from any of the first to third comparators 155a to 155c, the first OR gate 157a generates a failure signal (high-level signal) indicating the occurrence of the potential failure in which any of the circuit terminals VS+, COM and IP+ (the sensor terminals Vs+, Com and Ip+, the electric wires 124, 125 and 126) is shorted to battery potential.

The second OR gate 157b implements logical OR operation of the failure signals from the fourth to sixth comparators 155d to 155f. Upon receipt of the failure signal from any of the fourth to sixth comparators 155d to 155f, the second OR gate 157b generates a failure signal (high-level signal) indicating the occurrence of the potential failure in which any of the circuit terminals VS+, COM and IP+ (the sensor terminals Vs+, Com and Ip+, the electric wires 124, 125 and 126) is shorted to ground potential.

The failure detection element 159 organizes the connection potential information according to the failure signals from the comparators 155a to 155f and the OR gates 157a and 157b to select among three operation modes: an active mode (A mode), a protect mode (P mode) and a non-active mode (NA mode) so that the ECU 180 controls the operations of the sensor control unit 130 in the selected operation mode.

The A mode is selected to conduct gas concentration detection under normal conditions without the occurrence of no potential failure in the gas sensor system 100 (the presence of no failure signal). In the A mode, the switch on-off signals are outputted from the ECU 180 to turn on the switches SW2, SW3, SW6 and SW7 and turn off the switches SW1, SW4 and SW5. The negative feedback loop of the sensor control unit 130 is then established so that the amplifier 136 performs a negative feedback control of the pumping cell current Ip using the output voltage of the sensing cell 119 as the feedback. The exhaust oxygen concentration (the air-fuel ratio) is detected according to the pumping cell current Ip for engine combustion control as explained above.

The P mode is selected to provide electrical protection to the gas sensor 110 upon detection of the potential failure in the gas sensor system 100 (in the presence of the failure signal). In the P mode, the switch on-off signals are outputted from the ECU 180 to turn off all of the switches SW1 to SW7. The gas sensor 110 becomes disconnected from the power supply circuit (the amplifiers 136, 139 and 140, the resistors R6 and R7, the constant current source 142 and the voltage clamp 144) of the sensor control unit 130 to interrupt the electrical connections between the gas sensor 110 and the sensor control unit 130 and cut off all of the current/voltage outputs from the sensor control unit 131 to the gas sensor 110. The gas sensor 110 is thus protected from excessive current flow or current flow in the wrong direction for prevention of deterioration or breakage of the gas sensor 110 even in the event of the potential failure in the electrical connections between the gas sensor 110 and the sensor control unit 130.

The NA mode is selected to carry out system failure diagnosis. In the NA mode, the switch on-off signals are outputted from the ECU 180 to turn on the switches SW1 and SW4 to SW7 and turn off the switches SW2 and SW3. When the switch SW3 is OFF, the negative feedback loop of the sensor control unit 130 becomes interrupted to cut off the output of the pumping cell current Ip from the amplifier 136 to the gas sensor 110. On the other hand, the diagnosis current is supplied from the amplifier 136 to each of the pumping cell 117 and the sensing cell 119 when the switch SW1 is ON. In this state, the system failure diagnosis is carried out by checking the potentials of the circuit terminals VS+, COM and IP+, generating the failure signals and diagnosing by the failure signals whether and which of the circuit terminals VS+, COM and IP+ is failing.

In order for the ECU 180 to allow easy failure detection and identification, the failure detection element 159 provides the connection potential information by selectively setting and clearing various flags such as a F-VBshort flag, a F-GNDshort flag, a F-VS+/VBshort flag, a F-COM/VBshort flag, a F-IP+/VBshort flag, a F-VS+/GNDshort flag and a F-COM/GNDshort flag based on the failure signals.

The F-VBshort flag is set to "1" at the time the failure signal is outputted from the first OR gate 157a to the failure detection element 159 i.e. when any of the circuit terminals VS+, COM and IP+ (the sensor terminals Vs+, Com and Ip+, the electric wires 124, 125 and 126) is judged as being shorted to battery potential. The F-VBshort flag is set to "0" at all other times.

The F-GNDshort flag is set to "1" at the time the failure signal is outputted from the second OR gate 157b to the failure detection element 159 i.e. when any of the circuit terminals VS+, COM and IP+ (the sensor terminals Vs+, Com and Ip+, the electric wires 124, 125 and 126) is judged as being shorted to ground potential. The F-GNDshort flag is set to "0" at all other times.

The F-VS+/VBshort flag is set to "1" at the time the failure signal is outputted from the first comparator 155a to the failure detection element 159 i.e. when the circuit terminal VS+ (the sensor terminal Vs+, the electric wire 126) is judged as being shorted to battery potential. The F-VS+/VBshort flag is set to "0" at all other times.

The F-COM/VBshort flag is set to "1" at the time the failure signal is outputted from the second comparator 155b to the failure detection element 159 i.e. when the circuit terminal COM (the sensor terminal Com, the electric wire 125) is judged as being shorted to battery potential. The F-COM/VBshort flag is set to "0" at all other times.

The F-IP+/VBshort flag is set to "1" at the time the failure signal is outputted from the third comparator 155c to the failure detection element 159 i.e. when the circuit terminal IP+ (the sensor terminal Ip+, the electric wire 124) is judged as being shorted to battery potential. The F-IP+/VBshort flag is set to "0" at all other times.

The F-VS+/GNDshort flag is set to "1" at the time the failure signal is outputted from the fourth comparator 155d to the failure detection element 159 i.e. the circuit terminal VS+ (the sensor terminal Vs+, the electric wire 126) is judged as being shorted to ground potential. The F-VS+/GNDshort flag is set to "0" at all other times.

The F-COM/GNDshort flag is set to "1" at the time the failure signal is outputted from the fifth comparator 155e to the failure detection element 159 i.e. when the circuit terminal COM (the sensor terminal Com, the electric wire 125) is judged as being shorted to ground potential. The F-COM/GNDshort flag is set to "0" at all other times.

Figure 3:
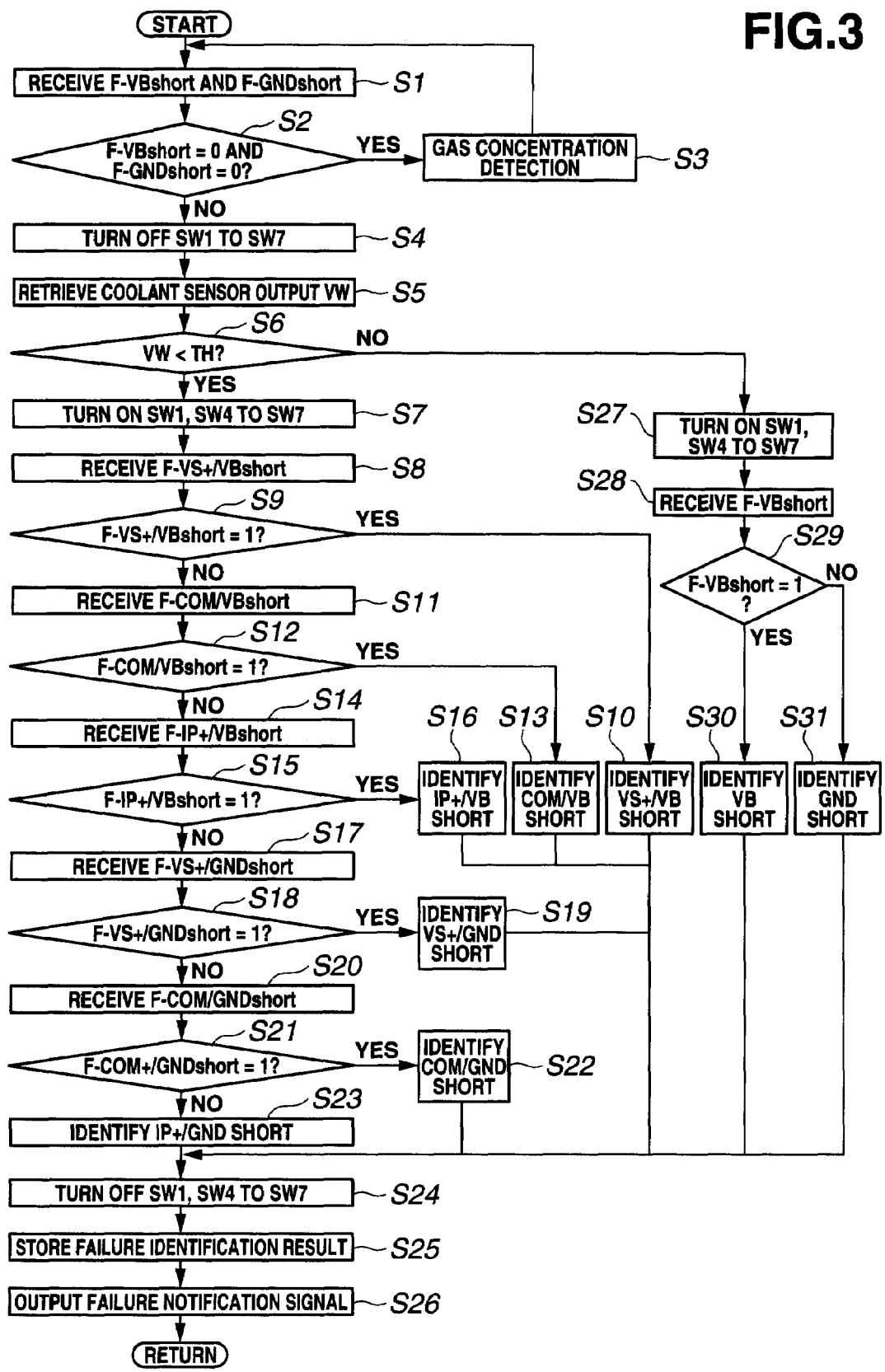
FIG. 3 is a flowchart of operations of the gas sensor system according to one exemplary embodiment of the present invention.

The operations (gas concentration detection and failure diagnosis) of the gas sensor system 100 are initiated by vehicle key actuation and executed through the following procedure as shown in FIG. 3.

At step S1, the engine control unit 180 receives the F-VBshort flag and the F-GNDshort flag from the failure detection element 159 of the sensor control circuit 131 by serial transmissions.

At step S2, the engine control unit 180 judges whether the F-VBshort flag and the F-GNDshort flag are set to zero. If F-VBshort flag=0 and F-GNDshort=0 (Yes at step S2), the engine control unit 180 decides that none of the circuit terminals VS+, COM and IP+ (the sensor terminals Vs+, Com and Ip+, the electric wires 124, 125 and 126) is shorted to battery or ground potential. The program control goes to step S3. If F-VBshort flag=1 and/or F-GNDshort=1 (No at step S2), the engine control unit 180 decides that either of the circuit terminals VS+, COM and IP+ (the sensor terminals Vs+, Com and Ip+, the electric wires 124, 125 and 126) is shorted to battery or ground potential. The program control goes to step S4.

At step S3, the engine control unit 180 performs normal gas concentration detection operations, i.e., judges whether the gas sensor 110 has been activated and, when the gas sensor 110 has been activated by a known activation judgment process, outputs the on-off signals to turn on the switches SW2, SW3, SW6 and SW7 and turn off the switches SW1, SW4 and SW5 so as to operate the sensor control unit 130 in the A mode for gas concentration detection and engine combustion control. The program control goes back to step S1 at appropriate interrupt.

At step S4, the engine control unit 180 outputs the on-off signals to turn off all of the switches SW1 to SW7 so as to operate the sensor control unit 130 in the P mode for electrical protection of the gas sensor 110. The program control then goes to step S5.

At step S5, the engine control unit 180 reads the output signal VW of the coolant temperature sensor 185 as the sensor temperature parameter.

At step S6, the engine control unit 180 judges whether the output VW of the coolant temperature sensor 185 is lower than a predetermined threshold temperature level TH. The threshold temperature level TH is set to e.g. 20° C. equivalent to a cold state of the engine where the gas sensor 110 has been sufficiently cooled to the predetermined temperature or lower. If VW<TH (Yes at step S6), the program control goes to step S7. If VW≧TH (No at step S6), the program control goes to step S27.

At step S7, the engine control unit 180 outputs the on-off signals to turn on the switches SW1 and SW4 to SW7 and turn off the switches SW2 and SW3 so as to operate the sensor control unit 130 in the NA mode for system failure diagnosis. At this time, the gas sensor 110 is in the low-temperature state of high internal resistance so as to produce a relatively large potential difference at the terminal VS+, COM, IP+ by the passage of the weak diagnosis current. The program control thus goes through steps S8 to S23 for detection and identification of the potential failure.

At step S8, the engine control unit 180 receives the F-VS+/VBshort flag from the failure detection element 159. The program control goes to step S9.

At step S9, the engine control unit 180 judges whether the F-VS+/VBshort flag is set to one. If F-VS+/VBshort flag=1 (Yes at step S9), the program control goes to step S10. If F-VS+/VBshort flag=0 (No at step S9), the program control goes to step S11.

At step S10, the engine control unit 180 identifies that the circuit terminal VS+ (the sensor terminal Vs+, the electric wire 126) is shorted to battery potential. Then, the program control goes to step S24.

At step S11, the engine control unit 180 receives the F-COM/VBshort flag from the failure detection element 159.

At step S12, the engine control unit 180 judges whether the F-COM/VBshort flag is set to one. If F-COM/VBshort flag=1 (Yes at step S12), the program control goes to step S13. If F-COM/VBshort flag=0 (No at step S12), the program control goes to step S14.

At step S13, the engine control unit 180 identifies that the circuit terminal COM (the sensor terminal Com, the electric wire 125) is shorted to battery potential. The program control goes to step S24.

At step S14, the engine control unit 180 receives the F-IP+/VBshort flag from the failure detection element 159. The program control goes to step S15.

At step S15, the engine control unit 180 judges whether the F-IP+/VBshort flag is set to one. If F-IP+/VBshort flag=1 (Yes at step S15), the program control goes to step S16. If F-IP+/VBshort flag=0 (No at step S15), the program goes to step S17.

At step S16, the engine control unit 180 identifies that the circuit terminal IP+ (the sensor terminal Ip+, the electric wire 124) is shorted to battery potential. The program control goes to step S24.

At step S17, the engine control unit 180 receives the F-VS+/GNDshort flag from the failure detection element 159.

At step S18, the engine control unit 180 judges whether the F-VS+/GNDshort flag is set to one. If F-VS+/GNDshort flag=1 (Yes at step S18), the program control goes to step S19. If F-VS+/GNDshort flag=0 (No at step S18), the program control goes to step S20.

At step S19, the engine control unit 180 identifies that the circuit terminal VS+ (the sensor terminal Vs+, the electric wire 126) is shorted to ground potential. The program control goes to step S24.

At step S20, the engine control unit 180 receives the F-COM/GNDshort flag from the failure detection element 159. The program control goes to step S21.

At step S21, the engine control unit 180 judges whether the F-COM/GNDshort flag is set to one. If F-COM/GNDshort flag=1 (Yes at step S21), the program control goes to step S22. If F-COM/GNDshort flag=0 (No at step S21), the program control goes to step S23.

At step S22, the engine control unit 180 identifies that the circuit terminal COM (the sensor terminal Com, the electric wire 125) is shorted to ground potential. The program control goes to step S24.

At step S23, the engine control unit 180 identifies that the circuit terminal IP+ (the sensor terminal Ip+, the electric wire 124) is shorted to ground potential. The program control goes to step S24.

At step S24, the engine control unit 180 outputs the on-off signals to turn off the switches SW1 and SW4 to SW7, i.e., turn off all of the switches SW1 to SW7 and exit from the NA mode. The program control goes to step S25.

At step S25, the engine control unit 180 stores therein the result of identification of the potential failure. The program control goes to step S26.

At step S26, the engine control unit 180 outputs a failure notification signal to generate an alarm etc. that informs a vehicle driver of the potential failure. After that, the program control goes back to step S1.

At step S27, the engine control unit 180 outputs the on-off signals to turn on the switches SW1 and SW4 to SW7 and turn off the switches SW2 and SW3 so as to operate the sensor control unit 130 in the NA mode for system failure diagnosis. At this time, the gas sensor 110 is in the high-temperature state of low internal resistance so that the potential difference developed at the terminal VS+, COM, IP+ by the passage of the weak diagnosis current is not so large. It is difficult in such a high-temperature state to identify what kind of the potential failure is occurring in which of the terminals VS+, COM and IP+, but possible to detect that any of the terminals VS+, COM and IP+ is shorted to battery or ground potential. The program control thus goes through steps S28 to S31 for detection of the potential failure.

At step S28, the engine control unit 180 receives the F-VBshort flag from the failure detection element 159. The program control goes to step S29.

At step S29, the engine control unit 180 judges whether the F-VBshort flag is set to one. If F-VBshort flag=1 (Yes at step S29), the program control goes to step S30. If F-VBshort flag=0 (No at step S29), the program control goes to step S31.

At step S30, the engine control unit 180 identifies that any one of the terminals VS+, COM and IP+ (the sensor terminals Vs+, Com and Ip+, the electric wires 124, 125 and 126) is shorted to battery potential. The program control goes to step S24.

At step S31, the engine control unit 180 identifies that any one of the terminals VS+, COM and IP+ (the sensor terminals Vs+, Com and Ip+, the electric wires 124, 125 and 126) is shorted to ground potential. The program control goes to step S24.

As described above, the system failure diagnosis undergoes the failure detection step (steps S1, S2 and S4) to detect the potential failure in any of the electrical connections between the gas sensor 110 and the sensor control unit 130 (the circuit terminals VS+, COM, IP+, the sensor terminals Vs+, Com, Ip+, the electric wires 124, 125, 126) and the sensor temperature determination step (steps S5 and S6) to judge whether the gas sensor 100 has been cooled to the predetermined temperature or lower with reference to the output VW of the coolant sensor 185 (the sensor temperature parameter). Upon detection of the potential failure in any of the electrical connections between the gas sensor 110 and the sensor control unit 130 under conditions that the gas sensor 110 has been cooled to the predetermined temperature or lower, the system failure diagnosis undergoes the failure identification step (steps S7 to S24) to output the weak diagnosis signal and thereby identify what kind of the potential failure is occurring in which of the electrical connections between the gas sensor 110 and the sensor control unit 130. It is therefore possible to diagnose the potential failure properly and concretely without deterioration and breakage of the gas sensor 110 by controlling the diagnosis signal to within the safe limits. In the present embodiment, the failure identification step is performed by comparing the potential of each electrical connection between the gas sensor 110 and the sensor control unit 130 with the upper and lower limit thresholds VBshort and GNDshort and judging that the electrical connection is shorted to battery potential when the connection potential is higher than the upper limit threshold VBshort and is shorted to ground potential when the connection potential is lower than the lower limit threshold GND short. This allows more proper diagnosis of the potential failure. Further, the gas sensor 110 is once disconnected from the power supply circuit (the amplifiers 136, 139 and 140, the resistors R6 and R7, the constant current source 142 and the voltage clamp 144) of the sensor control unit 130 to cut off voltage/current supply from the power supply circuit to the gas sensor 110 upon detection of the potential failure. When the gas sensor 110 is judged as being cooled to the predetermined temperature or lower, the gas sensor 110 is connected with the part of the power supply circuit (the amplifier 139 and the resistors R6 and R7) to output the diagnosis signal during the failure identification step. This makes it possible to provide electrical protection to the gas sensor 110 so as to prevent the gas sensor 110 from deterioration and breakage in the event of the potential failure.

The entire contents of Japanese Patent Application No. 2006-146087 (filed on May 26, 2006) are herein incorporated by reference.

Although the present invention has been described with reference to the above embodiment of the invention, the invention is not limited to this specific exemplary embodiment. Various modification and variation of the embodiment described above will occur to those skilled in the art in light of the above teaching. The scope of the invention is defined with reference to the following claims.

What is claimed is:

1. A gas sensor system with a failure diagnostic function, comprising:
   a gas sensor capable of producing an output signal responsive to the concentration of a specific gas component in measurement gas;
   a gas concentration determination device that makes electrical connections to the gas sensor and determines the concentration of the specific gas component according to the output signal of the gas sensor;
   a failure detection device that detects the occurrence of a potential failure in any one of the electrical connections;
   a sensor temperature determination device that judges whether the gas sensor has been cooled to a predetermined temperature or lower with reference to a sensor temperature parameter; and
   a failure identification device that, when the gas sensor is judged as being cooled to the predetermined temperature or lower, outputs a diagnosis signal to the gas sensor, measures potentials of the respective electrical connections under the diagnosis signal and identifies said any one of the electrical connections in which the potential failure is occurring based on the measured potentials.

2. A gas sensor system according to claim 1, wherein the failure identification device judges that said any one of the electrical connections is shorted to battery potential when the potential of said any one of the electrical connections is higher than an upper limit threshold and that said any one of the electrical connections is shorted to ground potential when the potential of said any one of the electrical connections is lower than a lower limit threshold.

3. A gas sensor system according to claim 1, wherein the gas concentration determination device has a power supply circuit to supply power to the gas sensor through the electrical connections; the failure detection device interrupts the electrical connections to disconnect the gas sensor from the power supply circuit upon detection of the potential failure; and the failure identification device connects the gas sensor with a part of the power supply circuit and outputs the diagnosis signal from said part of the power supply circuit.

4. A failure diagnosis method for a gas sensor system, the gas sensor system having a gas sensor capable of producing an output signal responsive to the concentration of a specific gas component in measurement gas; a gas concentration determination device that makes electrical connections to the gas sensor and determines the concentration of the specific gas component according to the output signal of the gas sensor; a failure detection device that detects the occurrence of a potential failure in any one of the electrical connections; a sensor temperature determination device that judges whether the gas sensor has been cooled to a predetermined temperature or lower with reference to a sensor temperature parameter; and a failure identification device that, when the gas sensor is judged as being cooled to the predetermined temperature or lower, outputs a diagnosis signal to the gas sensor, measures potentials of the respective electrical connections under the diagnosis signal and identifies said any one of the electrical connections in which the potential failure is occurring based on the measured potentials; the failure diagnosis method comprising:
   detecting the occurrence of the potential failure in any one of the electrical potentials;
   judging whether the gas sensor has been cooled to a predetermined level or lower with reference to the sensor temperature parameter;
   when the gas sensor is judged as being cooled to the predetermined level or lower, outputting the diagnosis signal to the gas sensor;
   measuring potentials of the respective electrical connections under the diagnosis signal; and
   identifying said any one of the electrical connections in which the potential failure is occurring based on the measured potentials.

5. A failure diagnosis method according to claim 4, wherein said identifying includes: comparing the potential of said any one of the electrical connections with upper and lower limit threshold; and judging that said any one of the electrical connections is shorted to battery potential when the potential of said any one of the electrical connections is higher than the upper limit threshold and that said any one of the electrical connections is shorted to ground potential when the potential of said any one of the electrical connections is lower than the lower limit threshold.

6. A failure diagnosis method according to claim 4, further comprising:
   interrupting the electrical connections to disconnect the gas sensor from a power supply circuit of the gas concentration determination device upon detection of the potential failure,
   wherein said outputting includes connecting the gas sensor with a part of the power supply circuit to output the diagnosis signal from said part of the power supply circuit.

* * * * *